(12) United States Patent
Gulani et al.

(10) Patent No.: US 9,640,069 B2
(45) Date of Patent: May 2, 2017

(54) QUANTIFYING MAGNETIC RESONANCE PARAMETERS

(71) Applicant: Case Western Reserve University, Cleveland, OH (US)

(72) Inventors: Vikas Gulani, Cleveland Heights, OH (US); Yong Chen, Cleveland Heights, OH (US); Nicole Seiberlich, Shaker Heights, OH (US); Mark Griswold, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 624 days.

(21) Appl. No.: 14/169,543

(22) Filed: Jan. 31, 2014

(65) Prior Publication Data

US 2014/0292330 A1    Oct. 2, 2014

Related U.S. Application Data

(60) Provisional application No. 61/806,907, filed on Mar. 31, 2013.

(51) Int. Cl.
*G08C 23/06* (2006.01)
*G01R 33/36* (2006.01)
(Continued)

(52) U.S. Cl.
CPC ............ *G08C 23/06* (2013.01); *A61B 5/0017* (2013.01); *A61B 5/0073* (2013.01);
(Continued)

(58) Field of Classification Search
CPC ...... A61B 5/0073; A61B 5/055; A61K 49/06; G01R 33/3614; G01R 33/3692;
(Continued)

(56) References Cited

U.S. PATENT DOCUMENTS

| 2008/0309336 A1* | 12/2008 | Griswold | ........... G01R 33/4824 |
| | | | 324/309 |
| 2010/0201363 A1* | 8/2010 | Griswold | ........... G01R 33/5611 |
| | | | 324/314 |

(Continued)

*Primary Examiner* — Rodney Bonnette
(74) *Attorney, Agent, or Firm* — Quarles & Brady LLP

(57) ABSTRACT

Example apparatus and methods provide improved spatial and temporal resolution over conventional magnetic resonance imaging (MRI) for a large (e.g., 500 cm$^3$) three dimensional (3D) volume. Example apparatus and methods reconstruct under-sampled 3D data associated with nuclear magnetic resonance (NMR) signals acquired from the volume using a 3D through-time non-Cartesian generalized auto-calibrating partially parallel acquisitions (GRAPPA) approach. The NMR signals are produced in response to a 3D non-Cartesian (e.g., stack-of-spirals) pulse sequence. Example apparatus and methods produce a quantified value for T1 relaxation, T2 relaxation, diffusion, or other NMR parameters in the volume from signal intensities in the data. The quantified value may describe, for example, a perfusion parameter, a blood flow parameter, a blood volume parameter, or other value. Greater precision is achieved for the NMR parameter in the volume as a result of the quantization performed on data acquired with greater spatial resolution and temporal resolution.

37 Claims, 10 Drawing Sheets

(51) Int. Cl.
*G01R 33/56* (2006.01)
*G01R 33/48* (2006.01)
*G01R 33/58* (2006.01)
*G01R 33/563* (2006.01)
*A61K 49/06* (2006.01)
*A61B 5/00* (2006.01)
*A61B 5/055* (2006.01)

(52) U.S. Cl.
CPC ............ *A61B 5/4244* (2013.01); *A61K 49/06* (2013.01); *G01R 33/3614* (2013.01); *G01R 33/3692* (2013.01); *G01R 33/4822* (2013.01); *G01R 33/56* (2013.01); *G01R 33/5608* (2013.01); *G01R 33/56366* (2013.01); *G01R 33/58* (2013.01); *A61B 5/055* (2013.01)

(58) Field of Classification Search
CPC  G01R 33/4822; G01R 33/56; G01R 33/5608; G01R 33/56366; G01R 33/58; G01R 33/4824
See application file for complete search history.

(56) References Cited

U.S. PATENT DOCUMENTS

| | | | |
|---|---|---|---|
| 2011/0089946 A1* | 4/2011 | Griswold | G01R 33/4824 324/309 |
| 2011/0093233 A1* | 4/2011 | Griswold | G01R 33/4824 702/106 |
| 2014/0015527 A1* | 1/2014 | Griswold | G01R 33/4826 324/309 |
| 2014/0296700 A1* | 10/2014 | Gulani | G01R 33/3614 600/414 |
| 2014/0296702 A1* | 10/2014 | Griswold | G01R 33/3614 600/416 |

* cited by examiner

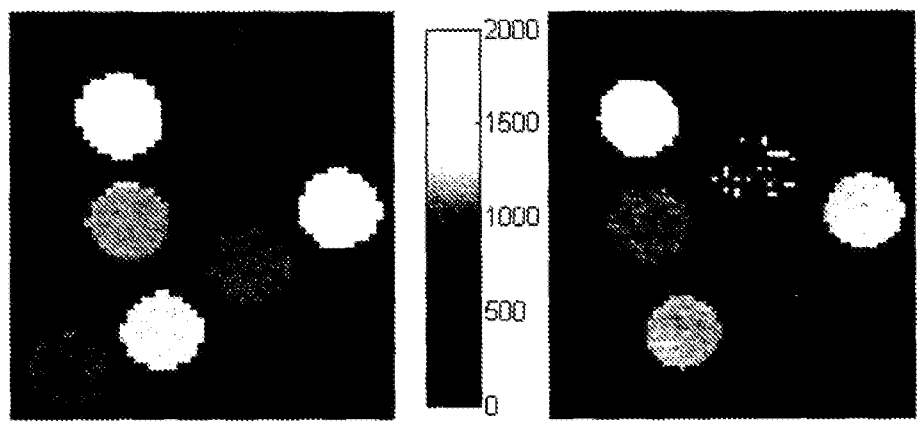
Figure 3A                    Figure 3B

QUANTIFYING MAGNETIC RESONANCE PARAMETERS

CROSS REFERENCE TO RELATED APPLICATIONS

This application claims the benefit of U.S. Provisional Patent Application 61/806,907 titled "Medical Imaging" filed Mar. 31, 2013.

FEDERAL FUNDING NOTICE

The invention was developed with federal funding supplied under Federal Grant Nos. R00EB011527, 2KL2RR00040 and 1R01DK098503-01A1 provided by the National Institute of Health (NIH). The Federal government has certain rights in the invention.

BACKGROUND

Quantitative knowledge of T1 relaxation time provides information that is useful for identifying and analysing a variety of pathological conditions. Quantitative knowledge of T1 relaxation also facilitates quantitative perfusion measurements. Conventionally, acquiring quantitative knowledge of T1 relaxation times has been challenging in large volumes that are affected by motion (e.g., abdomen). Conventional attempts to acquire full volume abdominal T1 maps in multiple breath holds have used a variable flip angle approach. Unfortunately, conventional variable flip angle approaches have been sensitive to B1 field inhomogeneity and have been compromised by motion between breathholds. Quantifying other magnetic resonance (MR) parameters (e.g., T2 relaxation, diffusion) has also been difficult, if even possible, to perform for large volumes that may experience motion.

Conventional attempts to acquire quantitative knowledge of MR parameters like T1 relaxation times may have included applying a Look-Locker pulse sequence, which is also known as a T1-scout method, to perform rapid T1 mapping. FIG. 1 illustrates a two dimensional Look-Locker pulse sequence. In general, a Look-Locker pulse sequence includes a preparation phase followed by multiple image acquisition phases. Unfortunately, due to the large volume to be covered, a Look-Locker pulse sequence applied with a Cartesian readout has not provided 3D T1 maps with adequate resolution in a clinically relevant scan time.

The Look-Locker method dates back to a spectroscopic one-shot method proposed by Look and Locker in 1968 (D. C. Look and D. R. Locker, Phys. Rev. Lett. 20, 987 (1968). Enhancements to the initial spectroscopic one shot method were described in Time Saving In Measurement Of NMR and EPR Relaxation Times, Look et al., The Review of Scientific Instruments, Volume 41, Number 2, February 1970. The paper described that by producing a train of absorption or dispersion signals (e.g., continuous-wave magnetic resonance) or free induction decays (e.g., pulsed magnetic resonance) it was possible to save time in spin-lattice relaxation measurements because it was not necessary to wait for equilibrium magnetization before initiating the train. The relaxation time was calculated from the train using a converging iteration.

The Look-Locker method was adapted to quickly sample the recovery after a preparation pulse during the recovery period or transient phase, as described in A Single-Scan Fourier Transform Method For Measuring Spin-Lattice Relaxation Times, Kaptein et al., Journal of Magnetic Resonance, Volume 24, Issue 2, November 1976, pages 295-300. The Kaptein method was then adapted by Graumann et al. to produce the TOMROP imaging sequence (T One by Multiple Readout Pulses). In the TOMROP approach, the multiple samples of a particular recovery after radio frequency (RF) preparation correspond to separate images. To acquire a complete data set for each image, the whole sequence is repeated numerous times, where a repetition fills the next line of k-space for an image. This may lead to lengthy acquisition times. This may also lead to the situation where different images have different unique delay times.

The Look-Locker (LL) method has been optimized and refined over the years for different purposes. For example, improved RF preparation pulses have been described by Been et al., in Serial Changes In The T1 Magnetic Relaxation Parameter After Myocardial Infarction In Man, BR Heart J 1988 29: 1-8. This paper described using a low field resistive nuclear magnetic resonance imaging system to study the in vivo changes in the relaxation parameter T1 in the heart. T1 maps were constructed from transverse and coronal images. Calculated T1 maps were obtained by an interleaved saturation-recovery and inversion-recovery pulse sequence with a time from inversion of 200 ms. Inversion was obtained with an adiabatic fast passage inverting pulse rather than the conventional 180 degree pulse. This adiabatic fast passage inverting pulse efficiently inverted all the nuclei in a volume for which a T1 map was to be produced.

The Look-Locker method has been adapted to include echo-planar imaging (EPI) in the inversion recovery as described by Ordidge et al., in High-speed multislice T1 mapping using inversion-recovery echo-planar imaging, Magn Reson Med 1990:16(2):238-245. Ordidge interleaved EPI readouts for eight different slices after an inversion pulse. The sequence was then repeated and the slice order was changed to achieve a range of inversion times for slices. Look-Locker with EPI was later applied in vivo in less than three seconds using a modified blipped EPI technique. While this technique was faster, precision and accuracy were compromised. Look-Locker with EPI facilitated acquiring an entire image at each point on a single recovery of longitudinal magnetisation after a saturation pulse. The Look-Locker with EPI technique was optimised as described by Freeman et al., in Optimization Of The Ultrafast Look-Locker Echo-Planar Imaging of T1 Mapping Sequence, Magnetic Resonance Imaging, Vol. 16, No. 7, pp 765-772, 1998. This paper described how the measurement of T1 was important for studying in-flow perfusion and for studying dynamic contrast agent techniques.

An LL-EPI sequence includes a preparation phase (e.g., inversion pulse) followed by multiple image acquisition units. An image acquisition unit includes a low flip-angle RF pulse (e.g., a magnetization sample pulse) and the EPI module. T1 maps are calculated by fitting the signal to an image, pixel by pixel, to the recovery equation integrated over the sample pulse slice profile. Adaptations to the LL method included the modified Look-Locker (MOLLI) method. Comparisons of the LL method and the MOLLI method have been described in, for example, Myocardial T1 Mapping With MRI: Comparison of Look-Locker and MOLLI Sequences, Nacif et al., Journal of Magnetic Resonance imaging, 34; 1367-1373 (2011).

Magnetic resonance imaging (MRI) provides highly detailed anatomical information. Dynamic contrast-enhanced (DCE) MRI monitors the transit of contrast materials (e.g., gadolinium (Gd) chelates) through various regions (e.g., kidneys, liver). MRI using DCE may experience several stages. For example, at a first time, a bolus of contrast agent may arrive at a first location and produce a series of enhancement effects. By analyzing the enhancement at various time points after administration of contrast agent, clinically relevant parameters including blood flow, perfusion, and blood volume may be measured. However, acquiring sufficient signals to perform quantitation that is sufficient to support meaningful functional analysis requires a combination of spatial resolution and temporal resolution that has not been conventionally available.

Conventionally, different methods have been used to quantify information acquired by MRI. These methods include the upslope method, semi-quantitative parametric methods, and de-convolution methods. Unfortunately, the temporal resolution provided by conventional MRI systems may not have been sufficient to support high resolution three-dimensional (3D) T1 mapping for a large volume (e.g., abdomen). Additionally, applying conventional under-sampling to improve temporal resolution may have negatively impacted spatial resolution to the point where image quality fell below a desired level.

A pulse sequence is a preselected set of defined RF and gradient pulses that may be repeated many times during a scan. The time interval between pulses and the amplitude and shape of the gradient waveforms control NMR signal reception. Pulse sequences are characterized by parameters including repetition time (TR), echo time (TE), inversion time (TI), flip angle (FA), and other parameters. Look-Locker as implemented in T1-scout is a gradient recalled echo (GRE) sequence. A gradient echo is generated using a pair of bipolar gradient pulses. There may be no refocusing 180 degree pulse and the data may be sampled during a gradient echo. The gradient echo is achieved by dephasing spins with a negatively pulsed gradient before the spins are rephased by an opposite gradient with opposite polarity, which generates the echo. An excitation pulse may be referred to as an alpha pulse $\alpha$. The $\alpha$ pulse tilts the magnetization by a flip angle typically between 0 degrees and 90 degrees. The flip angle may be varied during data acquisition. In an ultrafast GRE sequence, TR and TE may be so short that tissues have a limited imaging signal and limited contrast. For example, TR may be less than 5 ms and TE may be less than 1 ms. Thus, in an ultrafast GRE sequence, magnetization may be prepared during the preparation module using, for example, a 180 degree inversion pulse. FIG. 2 shows an example ultrafast GRE pulse sequence. Look-Locker may also be implemented as, for example, an inversion recovery (IR) sequence. Unlike conventional inversion recovery (IR) sequences, multiple lines in k-space may be acquired after a single inversion pulse.

Conventional studies of large volumes have typically employed T1-weighted, GRE sequences. T1 refers to spin-lattice relaxation, T2 refers to spin-spin relaxation. 3D acquisitions may have provided continuous coverage of a volume but only at the expense of longer acquisition times. When longer acquisition times are required, issues associated with movement in the volume are exacerbated. 3D T1 mapping within one breath-hold has typically been challenging. Thus, two-dimensional (2D) images have typically been acquired with higher temporal and spatial resolution. However, the 2D image approach may have been limited to a single representative slice or selected slices, which precluded whole volume analysis. Achieving higher temporal and spatial resolution facilitates achieving greater precision, accuracy, and image quality.

Kinetic modeling involves converting an MRI signal into a gadolinium (Gd) concentration. This conversion has been challenging because magnetic resonance (MR) signal intensity varies with contrast agent concentration, pulse sequence parameters, pre-contrast relaxation times, blood flow velocity, and other factors. Additionally, the relationship between signal and concentration is non-linear. Conventional spatial and temporal resolution may have been insufficient to provide adequate signal for meaningful functional analysis involving kinetic modeling.

BRIEF DESCRIPTION OF THE FIGURES

FIGS. 3A and 3B illustrate maps of multi-compartment phantoms.

DETAILED DESCRIPTION

Figure 1:
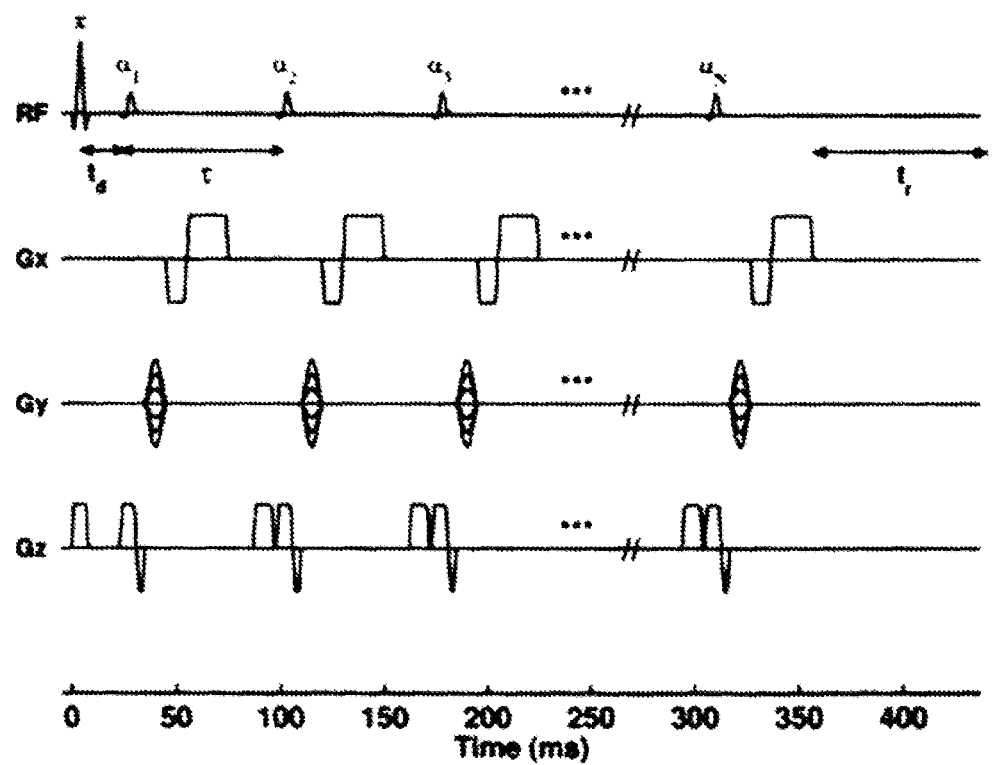
FIG. 1 illustrates a two dimensional Look-Locker pulse sequence.
Figure 2:
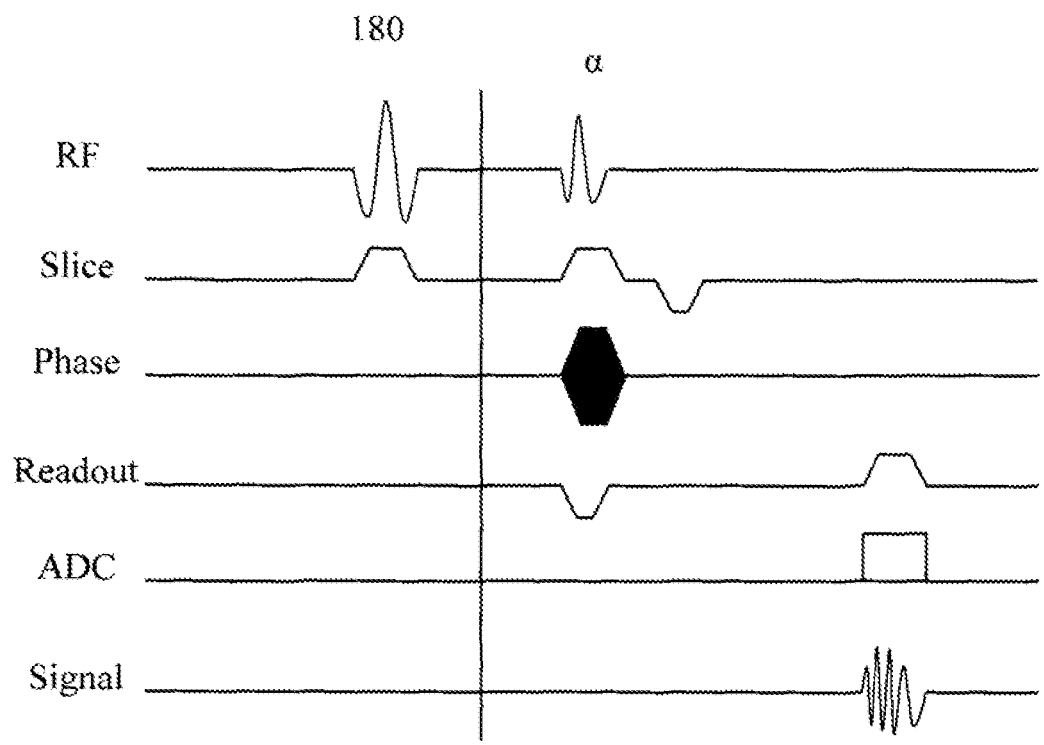
FIG. 2 illustrates an ultrafast gradient recalled echo (GRE) pulse sequence.

Example apparatus and methods perform highly under-sampled non-Cartesian acquisitions using through-time non-Cartesian generalized auto-calibrating partially parallel acquisitions (GRAPPA) reconstructions to acquire quantitative knowledge of MR parameters (e.g., T1 relaxation time, T2 relaxation time, diffusion) in a volume. In one embodiment, a Look-Locker method with non-Cartesian (e.g., stack-of-spirals) k-space acquisition may be used to acquire data with improved spatial resolution and temporal resolution from which quantified data having a desired precision can be acquired in a clinically relevant time frame (e.g., less than one breath hold). This embodiment may facilitate quantifying T1 relaxation time.

Sample data were acquired using a Siemens 1.5T Espree scanner with 12 receive channels. An inversion-recovery Look-Locker method was combined with a stack-of-spirals acquisition trajectory and with through-time non-Cartesian GRAPPA to accelerate data acquisition. In one sample data acquisition, the scan was divided into four inversion recovery periods with a pause between inversion recovery periods. The inversion recovery periods may be, for example, 2.7 seconds and the pauses may be, for example, 3.5 seconds. Different numbers of inversion recovery periods may be used. Inversion recovery periods of different lengths may be used. Pauses of different lengths may be used between inversion recovery periods. In one sample data acquisition, partitions were divided into segments and acquired in an interleaved manner. In one example, 24 partitions (32 total partitions, partial Fourier 6/8) were divided into four segments and acquired using 48 spiral interleaves in-plane to satisfy the Nyquist criterion. Different numbers of partitions and different numbers of interleaves may be used in different examples. To accelerate scanning, a reduction factor of four was used in-plane. Different reduction factors may be employed in different examples. The data was reconstructed using 3D through-time non-Cartesian GRAPPA. In one example, a GRAPPA kernel size of 2×3 was used in the spiral arm by readout direction. Different kernel sizes may be used in different acquisitions. A reference scan of eight fully sampled 3D volumes was acquired to calculate GRAPPA weights.

Sample data were acquired using different imaging parameters. For example, T1-weighted 3D volumes were analyzed with inversion times ranging from 240 to 2600 ms. Example imaging parameters included field of view (FOV) of 40×40 cm and a matrix size of 208×208, which yielded an effective in-plane resolution of 1.9 mm. Other example imaging parameters included repetition time (TR) of 4.5 ms, echo time (TE) of 0.6 ms, flip angle (FA) of 7 degrees and a partition thickness of 4 mm. Different imaging parameters may be used in different acquisitions.

Acquiring the under-sampled data is just part of the procedure for producing quantified data concerning an MR parameter (e.g., T1 relaxation time) in a volume. In one example, when a contrast agent is employed, the magnetic resonance (MR) signal data is quantified by converting signal intensity in the MR signal data to contrast agent concentration. In one example, to quantify results, signal intensity values may be converted to contrast agent concentration based, at least in part, on reference or calibration values provided from imaging of reference samples. The reference samples may be, for example, vials with known concentrations of the contrast agent. With quantified concentration values available, concentration time courses may be produced and then employed to estimate or illustrate parameters including, for example, perfusion, blood flow, blood volume, or other parameters. The parameters may be estimated using, for example, a non-linear least squares fit approach, the upslope method, semi-quantitative parametric methods, and de-convolution methods.

Producing quantified data facilitates producing outputs that may not be available to conventional systems. In one embodiment, a pixel-wise parameter mapping may be performed. Pixel-wise parameter mapping may produce a viewable parameter map that illustrates a desired parameter. The pixel-wise parameter mapping may be segmented by thresholding signal intensity values in a frame at different points.

FIG. 3A illustrates a T1 map of multi-compartment phantoms acquired using an inversion-recovery single-echo spin echo with TR=6 s. FIG. 3B illustrates a corresponding T1 map of the multi-compartment phantoms acquired using an example Look-Locker inversion-recovery stack-of-spirals method. Note the agreement between the results of the two methods.

Figures 4A, 4B, 4C, 4D:
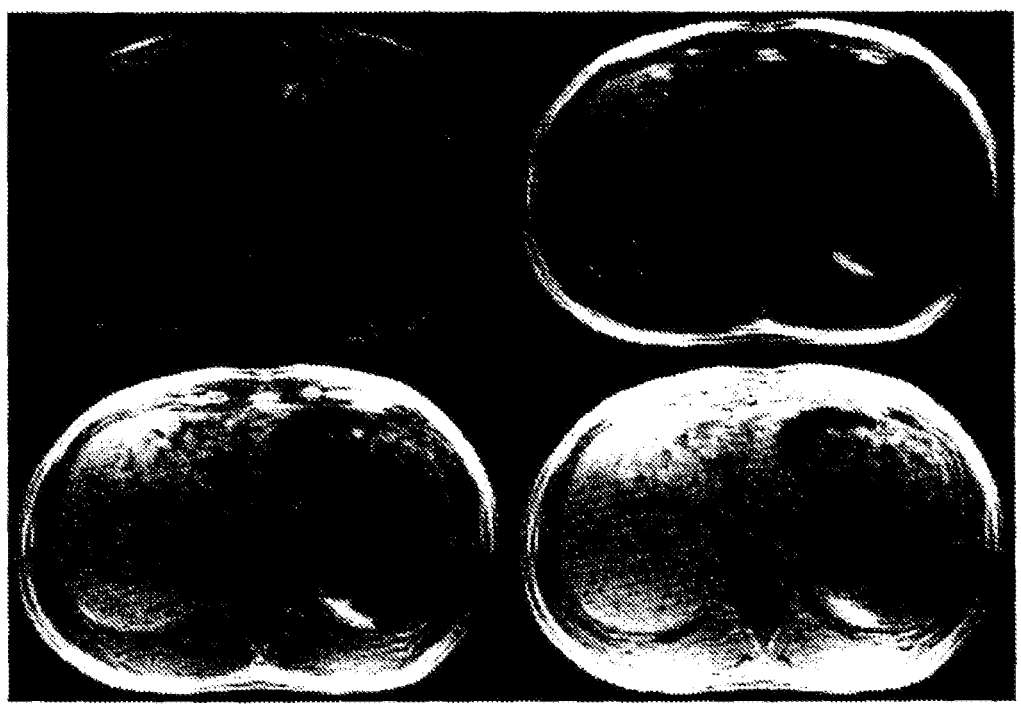
FIGS. 4A-4D illustrate T1-weighted images of one slice at different inversion times.
Figure 5:
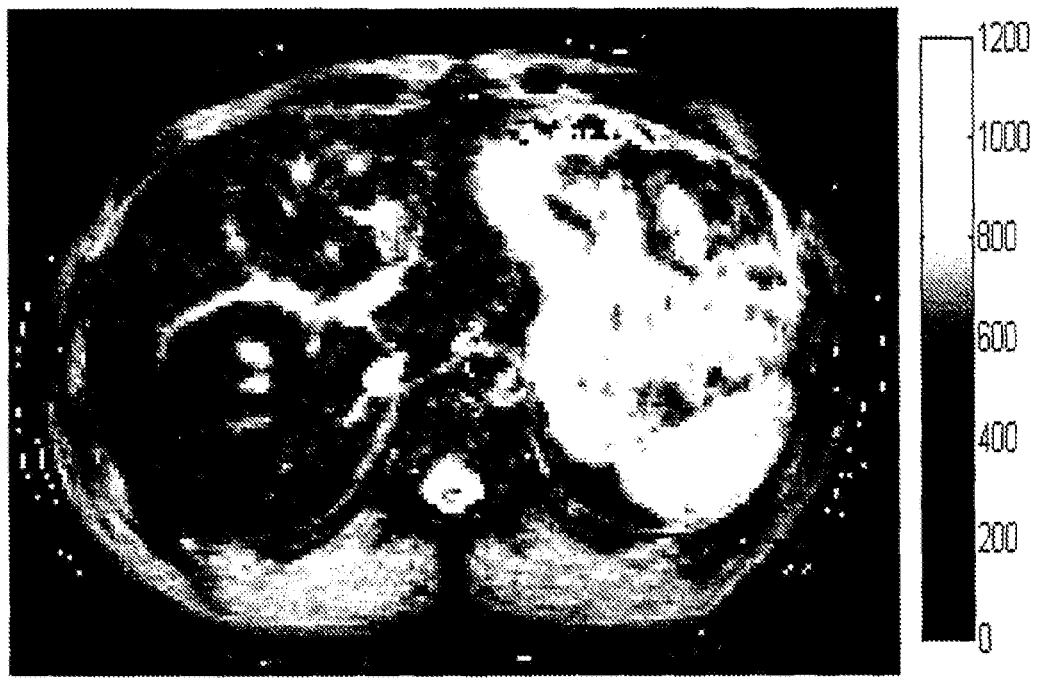
FIG. 5 illustrates a T1 map corresponding to T1-weighted images in FIGS. 4A-4D.

FIGS. 4A through 4D illustrate representative T1-weighted images along various points on the inversion recovery curve. FIG. 4A illustrates a T1-weighted image of a slice at an inversion time of 243 ms. FIG. 4B illustrates a T1-weighted image of a slice at an inversion time of 587 ms. FIG. 4C illustrates a T1-weighted image of a slice at an inversion time of 931 ms. FIG. 4D illustrates a T1-weighted image of a slice at an inversion time of 2652 s. FIG. 5 illustrates a T1 map corresponding to a single slice acquired from a normal subject. The results illustrated in FIGS. 3A through 5 demonstrate that example methods and apparatus can produce, in a period of time that is shorter than a typical breath hold, accurate, high resolution 3D large volume (e.g., abdominal) T1 mapping by using Look-Locker methods combined with stack-of-spirals trajectories and through-time non-Cartesian GRAPPA. The resulting images do not require B1 mapping or image registration. In different embodiments, the Look-Locker pulse sequence may be combined with the 3D through-time GRAPPA approach to quantize other MR parameters.

Figure 6:
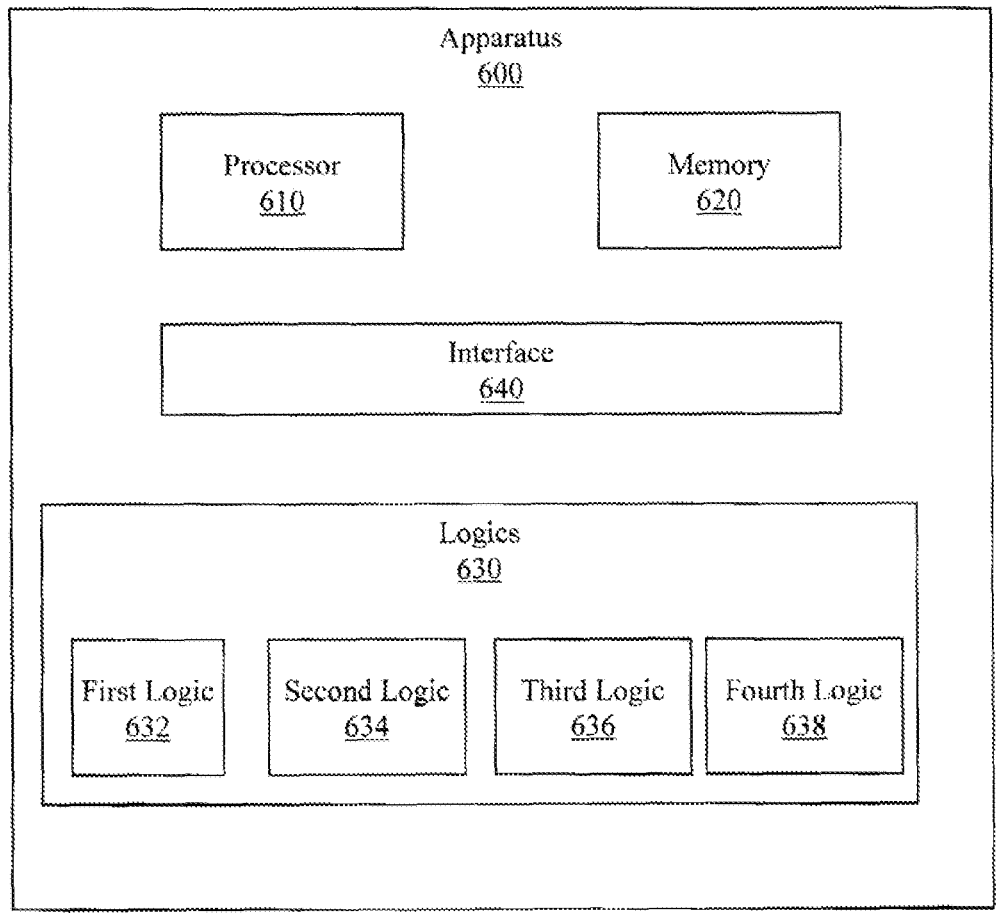
FIG. 6 illustrates an example apparatus associated with quantifying a magnetic resonance parameter using a Look-Locker method with 3D through-time non-Cartesian GRAPPA.

FIG. 6 illustrates an apparatus 600 for performing MRI-based quantitative analysis using a 3D through-time non-Cartesian GRAPPA approach for analyzing data acquired during a non-Cartesian (e.g., stack-of-spirals) Look-Locker procedure. Apparatus 600 includes a processor 610, a memory 620, a set 630 of logics, and an interface 640 to connect the processor 610, the memory 620, and the set 630 of logics. In one embodiment, apparatus 600 may be a special purpose computer that is created as a result of programming a general purpose computer. In another embodiment, apparatus 600 may include special purpose circuits that are added to a general purpose computer to produce a special purpose computer.

Apparatus 600 may include a first logic 632 that is configured to cause a volume to produce NMR signals in response to applying RF energy to the volume according to a 3D Look-Locker pulse sequence. In one embodiment, first logic 632 may be configured to control an MRI apparatus to apply the 3D Look-Locker pulse sequence to the volume. Recall that a Look-Locker pulse sequence includes a preparation phase and multiple image acquisition units per preparation phase. In one embodiment, the pulse sequence may be a "superfast" pulse sequence. With reference to a 3D Look-Locker pulse sequence, superfast refers to the TR being less than 4.5 ms and the TE being less than 0.6 ms. In different embodiments the Look-Locker pulse sequence may be an IR sequence, or a GRE sequence. The volume may be, for example, a human abdomen.

Apparatus 600 may also include a second logic 634 that is configured to acquire under-sampled 3D data associated with NMR signals from the volume. The under-sampled 3D data may be acquired according to a non-Cartesian acquisition trajectory. The non-Cartesian acquisition trajectory may be, for example, a stack-of-spirals trajectory, a stack-of-stars trajectory, or other trajectory. In one embodiment, the NMR signals are produced and acquired in less than twenty seconds. In another embodiment, the NMR signals are produced and acquired in less than ten seconds. In yet another embodiment, the NMR signals are produced and acquired in less than five seconds. In one embodiment, NMR signals are produced and acquired in less than V/20 seconds, where V describes the size of the volume in cubic centimeters. To speed acquisition, the second logic 634 may be configured to under-sample a partition in the volume by a reduction factor R. The partition may be, for example, a slice. The Look-Locker pulse sequence may partition the volume into partitions of different thicknesses. In one embodiment, the Look-Locker pulse sequence may have a partition thickness of less than 5 mm. In one embodiment R may be less than sixteen, in another embodiment R may be less than eight, and in another embodiment R may be less than four.

The Look-Locker pulse sequence may have different pulse sequence parameters. In one example, the Look-Locker pulse sequence may have an inversion time in the range of 240 ms to 2600 ms. Other ranges may be employed in other examples. In one embodiment, the Look-Locker pulse sequence may have a repetition time (TR) of less than 4.5 ms and an echo time (TE) of less than 0.6 ms. Other TR and TE may be employed in other examples. In one embodiment, the Look-Locker pulse sequence may have a flip angle (FA) of less than 8 degrees. Other FA may be employed in other examples.

Apparatus 600 may include a third logic 636 that is configured to reconstruct the under-sampled 3D data into reconstructed 3D data using 3D through-time non-Cartesian GRAPPA. Apparatus 600 may include a fourth logic 638 that is configured to produce a quantified value for an MR parameter (e.g., T1 relaxation) in the volume based, at least in part, on signal intensity in the reconstructed 3D data. The quantified value may be produced using techniques including, for example, a non-linear least squares fit approach, the upslope method, semi-quantitative parametric methods, and de-convolution methods.

Figure 7:
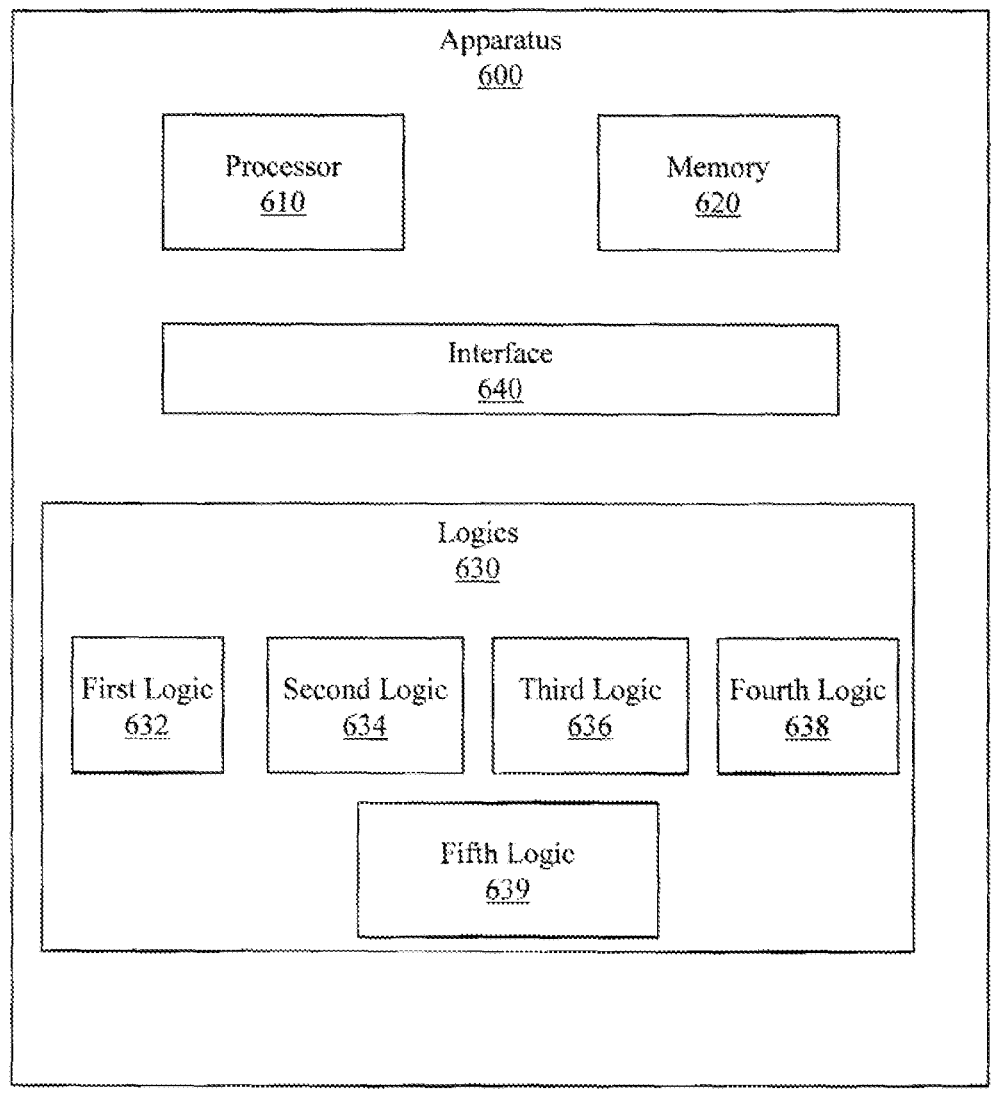
FIG. 7 illustrates an example apparatus associated with quantifying a magnetic resonance parameter using a Look-Locker method with 3D through-time non-Cartesian GRAPPA.

FIG. 7 illustrates another embodiment of apparatus 600. This embodiment of apparatus 600 includes a fifth logic 639 that is configured to produce a map from the quantified value for the MR parameter. In one embodiment, fifth logic 639 produces the map without performing B1 mapping and without performing image registration. The fifth logic 639 may also be configured to produce and display a viewable parameter map of the MR parameter. The fifth logic 639 may also be configured to produce a pixel-wise parameter map from the viewable parameter map.

Figure 8:
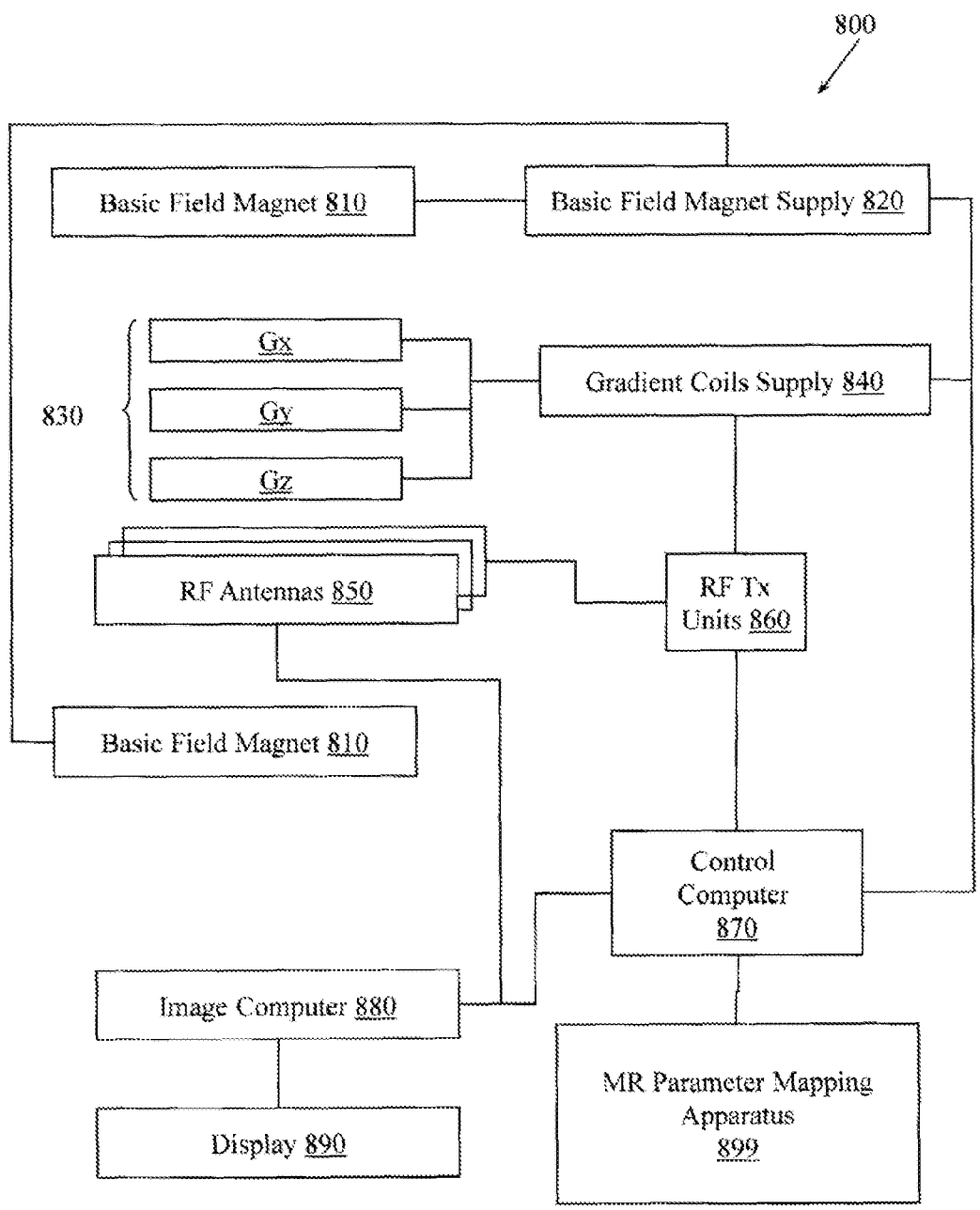
FIG. 8 illustrates an MRI apparatus configured to quantify a magnetic resonance parameter using a Look-Locker method with 3D through-time non-Cartesian GRAPPA.

FIG. 8 illustrates an MRI apparatus 800. MRI apparatus 800 is configured with a mapping apparatus 899 that is configured to quantify a magnetic resonance parameter (e.g., T1 relaxation) using a Look-Locker method with 3D through-time non-Cartesian GRAPPA. The mapping apparatus 899 may be configured with elements of example apparatus described herein or may perform example methods described herein, in one embodiment, mapping apparatus 899 may provide means for acquiring NMR signal data from a volume in response to apparatus 800 applying a 3D non-Cartesian Look-Locker MRI pulse sequence to the volume. Mapping apparatus 899 may also provide means for producing a quantified value of the MR parameter in the volume from the NMR signal. The quantified value of the MR parameter may be computed as a function of data reconstructed from the NMR signal data using 3D through-time non-Cartesian GRAPPA. Mapping apparatus 899, image computer 800, and display 890 may also provide means for displaying an image that includes a representation of the quantified value. The image may be, for example, a 3D T1 map, or other image.

The apparatus 800 includes a basic field magnet(s) 810 and a basic field magnet supply 820. Ideally, the basic field magnets 810 would produce a uniform $B_0$ field. However, in practice, the $B_0$ field may not be uniform and may vary over an object being imaged by the MRI apparatus 800. MRI apparatus 800 may include gradient coils 830 configured to emit gradient magnetic fields like $G_S$, $G_P$ and $G_R$ or Gx, Gy, and Gz. The gradient coils 830 may be controlled, at least in part, by a gradient coils supply 840. In some examples, the timing, strength, and orientation of the gradient magnetic fields may be controlled, and thus selectively adapted, during an MRI procedure.

MRI apparatus 800 may include a set of RF antennas 850 that are configured to generate RF pulses and to receive resulting NMR signals from an object to which the RF pulses are directed. In one embodiment, the RE antennas 850 are arranged as an array of parallel transmission coils that are individually controllable. How the pulses are generated and how the resulting MR signals are received may be controlled and thus may be selectively adapted during an MR procedure. Separate RF transmission and reception coils can be employed. The RF antennas 850 may be controlled, at least in part, by a set of RF transmission units 860. An RF transmission unit 860 may provide a signal to an RF antenna 850. The RF transmission unit 860 may provide different signals to different RF antennas to produce different RF excitations from the different members of the array of parallel transmission coils. In one example, the different RF excitations may have different flip angles and different TRs.

The gradient coils supply 840 and the RF transmission units 860 may be controlled, at least in part, by a control computer 870. In one example, the control computer 870 may be programmed to control an NMR device as described herein. Conventionally, the magnetic resonance signals received from the RF antennas 850 can be employed to generate an image and thus may be subject to a transformation process like a two dimensional fast Fourier transform (FFT) that generates pixilated image data. The transformation can be performed by an image computer 880 or other similar processing device. The image data may then be shown on a display 890. While FIG. 8 illustrates an example MRI apparatus 800 that includes various components connected in various ways, it is to be appreciated that other MRI apparatus may include other components connected in other ways.

Conventional GRAPPA generates uncombined coil images for each coil in an array of receive coils used by a parallel magnetic resonance imaging (pMRI) apparatus. GRAPPA reconstructs missing lines in coil elements by forming linear combinations of neighboring lines to reconstruct individual missing data points. The weights for these linear combinations are derived by forming a fit between additionally acquired lines using a pseudo-inverse operation. GRAPPA is described in Griswold, et al., Magn Reson Med, Vol. 47, Issue 6, Pg. 1202-1210 (2002).

Conventional non-Cartesian GRAPPA acquires data and makes a reconstruction kernel comprised of GRAPPA weights. The reconstruction kernel is used to reconstruct acquisition path elements acquired during a radial reconstruction. The quality of a non-Cartesian GRAPPA reconstruction depends, at least in part, on whether a suitable reconstruction kernel that corresponds to an acquisition path element being reconstructed is available. Radial GRAPPA is described in Griswold et al., Proc. ISMRM 11, 2003, p2349. While the radial trajectory provides a useful test bed for non-Cartesian trajectories, other non-Cartesian trajectories are possible. Non-Cartesian GRAPPA can include acquisition paths that include, for example, spiral acquisitions, rosette acquisitions, and other acquisitions.

Through-time GRAPPA facilitates achieving high frame rates and high resolution in applications like functional imaging of the kidney. Through-time non-Cartesian GRAPPA is described in US Patent Application 2011/0089946, now U.S. Pat. No. 8,542,012, filed Jan. 26, 2010 titled "Through-time Non-Cartesian GRAPPA Calibration". GRAPPA reconstruction depends on having useful GRAPPA weights to support the reconstruction. Computing a useful set of GRAPPA weights requires a threshold amount of differentiated calibration data. Differentiated calibration data is acquired from unique calibration frames. By applying a gradient in a direction perpendicular to a non-Cartesian encoded plane during acquisition of a fully-sampled calibration data scan, the data from the different applications of the perpendicular gradient or different partitions in the fully-sampled calibration data scan can be treated as unique calibration frames if at least three differences are produced in consecutive TRs. Therefore, fewer repetitions of the fully sampling calibration data scans are required to acquire the threshold amount of calibration data for computing GRAPPA weights. In one embodiment, consistently changing the perpendicular gradient in a known and controlled manner facilitates acquiring groups of lines having similar or identical gradients. While "lines" are described, one skilled in the art will appreciate that other acquisition elements (e.g., rays, spirals) may be similarly acquired.

Example apparatus and methods may acquire calibration data at different points in time (e.g., through time) and then perform a through-time GRAPPA calibration using the calibration data acquired at the different points in time. Useful calibration data can be derived from different groups of lines when the groups can be treated as separate time frames for the through-time calibration. The utility of the calibration data also depends on the calibration data being incoherent with image data acquired from a portion of an object that is moving. If the calibration data is acquired under similar conditions at different times, then the calibration data may be synchronized with the portion of the moving object rather than being incoherent with the portion of the moving object. When a calibration dataset (e.g., stack-of-stars) is phase encoded in a direction perpendicular to the non-Cartesian encoded plane, different groups experience a different gradient in the direction perpendicular to the non-Cartesian scan plane. When the gradient is changed in an orthogonal direction through time, the effective appearance of different groups of lines is different. Since different groups of lines have different effective appearances, the different groups of lines can be used to calibrate for through-time GRAPPA.

In one example, an under-sampled stack-of-spirals dataset may be acquired in a segmented fashion during a single breath hold or during free-breathing. The data set may be reconstructed using through-time GRAPPA. For the calibration, multiple groups of lines acquired over multiple repetitions may be used to calibrate the individual in-plane GRAPPA weights and the through plane data. This facilitates reducing the number of fully-sampled repetitions employed for the reconstruction.

In GRAPPA, a missing k-space data point in a single coil can be reconstructed by a combination of acquired data points from other coils. The conventional one dimensional (1D) GRAPPA reconstruction is described by:

$$S(k_y + m\Delta k_y) = \hat{G}_{y,m} \cdot S(k_y), m=1 \ldots (R-1)$$

The vector $S(k_y)$ contains the acquired signal associated with the k-space location $k_y$, the signal being received in $N_c$ coils. The vector $S(k_y)$ has the length $N_c$. The vector $S(k_y + m\Delta k_y)$, of length $N_c$, contains the reconstructed signals at location $k_y + m\Delta k_y$ in the $N_c$ coils.

The weighting matrix $\hat{G}_{y,m}$, with size $N_c \times N_c$, contains coil weighting factors. In conventional GRAPPA, a weighting matrix can be calculated if fully-sampled reference data are available such that $S(k_y)$ and $S(k_y + m\Delta k_y)$ are known for desired shifts m, by solving:

$$\hat{G}_{y,m} = S(k_y + m\Delta k_y) \cdot (S(k_y)^H S(k_y))^{-1} (S(k_y)^H)$$

However, this conventional GRAPPA approach required a complete set of reference data that satisfied the Nyquist criterion and, as described, above, acquiring multiple complete sets of reference data may be impractical in some applications. Therefore, techniques like two dimensional through time calibration were developed.

Two dimensional through time calibration used an incomplete reference data set to calculate reconstruction parameters based on fitting neighboring k-space lines. While analyzing the relationship between adjacent lines in a reference data set theoretically provided knowledge to do complete reconstruction in an under-sampled frame, there was also information available about other relationships between lines in the reference data set. Therefore, in one example that used all available information, second relationships were used to fill missing lines to facilitate computing reconstruction parameters. The computed reconstruction parameters were then applied to the raw data of an under-sampled individual frame to grow a reference data set by filling in missing lines and finally to obtain a final data set. While a complete data, set is described, it is to be appreciated that a less than complete data set may be created by iteratively applying information gathered from relationships between lines in the under-sampled data space. Additionally, when parallel processing was available, a reference data set may be grown in parallel.

Consider the following equation for determining a signal at a missing location $S_j(k_y + m\Delta k_y)$ based on an acquired signal:

$$S_j(k_y + m\Delta k_y) = \sum_{l=1}^{L} n(j, b, l, m) S_l(k_y + bA\Delta k_y)$$

$S_j(k_y)$ contains individual coil signals, $n(j, b, l, m)$ represents reconstruction weights. The acquired signal at some position k in k-space in a coil j of the array is given by $S(j, k)$. k is a vector that specifies the multi-dimensional location in k-space ($k_x$, $k_y$, $k_z$). For L coils, the 2D matrix is sized $L \times N_k$, where $N_k$ is the total number of k-space points in the image. Thus, the GRAPPA formulation could be converted to:

$$S_{(j,k+\Delta k)} = G_1 S_{(j,k)}$$

where the set of weights $G_1$ corresponds to $n(j, b, l, m)$ for b=1, m=1, so that the individual rows of the $L \times LG$ matrix are the GRAPPA weights used to reconstruct the shifted line $S_{(j,k+\Delta k)}$ in each respective coil.

These calculations were used to describe an infinitesimal shift to derive a set of weights $G_d$ with a small shift of δ. The generalization was described according to:

$$S_{(j,k+\delta)} = G_\delta S_{(j,k)}$$

Re-gridding has been employed in non-Cartesian GRAPPA. Non-Cartesian GRAPPA improves on conventional pMRI processing using non-Cartesian trajectories. An under-sampled non-Cartesian (e.g., radial) acquisition will not acquire every possible ray in a radial pattern. Assuming that 360 rays are available, one for each degree in a circle associated with a radial pattern, a fully-sampled data set would require a ray at multiple rotations (e.g., 0 degrees, 1 degree, 2 degrees). However, in an under-sampled radial acquisition, less than every ray would be acquired. For example, rays may be acquired at 0 degrees, 2 degrees, 4 degrees, and at other angles. Therefore there are rays missing at 1 degrees, 3 degrees, and at other angles. However, these missing rays can be filled in using conventional GRAPPA techniques. Similarly, an under-sampled spiral or other non-Cartesian acquisition will not acquire every possible "line".

Calibration data may be acquired according to a plan that acquires acquisition path elements that are in the same configuration as acquisition path elements that will be used in a reconstruction. When data is acquired through time (e.g., at 1 second intervals), the reconstruction kernel may be exact for the acquisition path elements that are acquired multiple times through time. By repeatedly acquiring calibration data for an acquisition path element at different points in time throughout a period of time, a point in k-space to be solved for using the reconstruction kernel can be successfully reconstructed based on the high quality calibration data. Consider a calibration data set that acquires a calibration spiral for 0 degrees rotation and for 5 degrees rotation at several points in time throughout the period of time. At each point in time there will be a spiral for zero degrees and a spiral for five degrees. While the calibration data set need not be fully-sampled, it will be configured to have the same configuration as the reconstruction kernel. This means that if a reconstruction will rely on spirals for 0 degrees, 5 degrees, 10 degrees, etc., then the calibration data set will acquire, through time, multiple copies of calibration data for the reconstruction kernel spirals. The reconstruction kernel constructed from these repeatedly acquired spirals can be very accurate. While spirals are described, one skilled in the art will appreciate that other non-Cartesian acquisition trajectories may be employed.

Performing a through-time GRAPPA calibration could also be referred to as calibrating the MRI with a set of calibration data acquired at different points over a period of time. An under-sampled data set can be reconstructed using selected weights associated with calibration data acquired at different points in time. For example, a reconstruction can use weights from an immediately preceding calibration data set, from an immediately following calibration data set, from a combination of the before and after calibration data sets, from all the calibration data sets, and from other combinations. A weight set for each missing point can be calibrated and applied separately.

Some portions of the detailed descriptions that follow are presented in terms of algorithms and symbolic representations of operations on data bits within a memory. These algorithmic descriptions and representations are used by those skilled in the art to convey the substance of their work to others. An algorithm is considered to be a sequence of operations that produce a result. The operations may include creating and manipulating physical quantities that may take the form of electronic values. Creating or manipulating a physical quantity in the form of an electronic value produces a concrete, tangible, useful, real-world result.

It has proven convenient at times, principally for reasons of common usage, to refer to these signals as bits, values, elements, symbols, characters, terms, numbers, and other terms. It should be borne in mind, however, that these and similar terms are to be associated with the appropriate physical quantities and are merely convenient labels applied to these quantities. Unless specifically stated otherwise, it is appreciated that throughout the description, terms including processing, computing, and determining, refer to actions and processes of a computer system, logic, processor, or similar electronic device that manipulates and transforms data represented as physical quantities (e.g., electronic values).

Example methods may be better appreciated with reference to flow diagrams. For simplicity, the illustrated methodologies are shown and described as a series of blocks. However, the methodologies may not be limited by the order of the blocks because, in some embodiments, the blocks may occur in different orders than shown and described. Moreover, fewer than all the illustrated blocks may be required to implement an example methodology. Blocks may be combined or separated into multiple components. Furthermore, additional or alternative methodologies can employ additional, not illustrated blocks.

Figure 9:
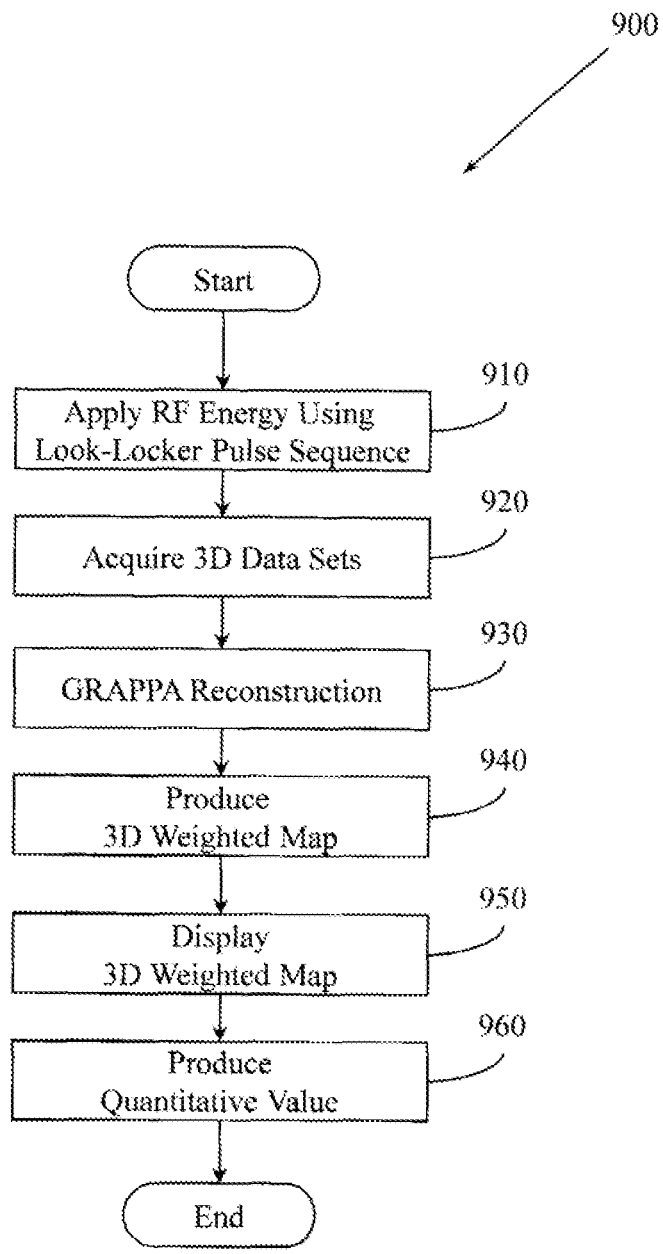
FIG. 9 illustrates a method associated with quantifying a magnetic resonance parameter using a Look-Locker method with 3D through-time non-Cartesian GRAPPA.

FIG. 9 illustrates an example method 900 associated with quantifying an MR parameter (e.g., T1 relaxation) using a Look-Locker method with 3D through-time non-Cartesian GRAPPA reconstruction. Method 900 includes, at 910, controlling an MRI apparatus to apply RF energy to a volume according to a non-Cartesian 3D Look-Locker (LL) pulse sequence that is configured to cause the volume to produce NMR signals. Recall that a Look-Locker pulse sequence includes a preparation phase and two or more image acquisition units per preparation phase. In one embodiment, the LL pulse sequence may be a superfast LL pulse sequence.

In different embodiments the Look-Locker pulse sequence may take different forms. In one embodiment, the Look-Locker pulse sequence may be an inversion recovery (IR) pulse sequence where the preparation phase includes an inversion pulse. The inversion pulse may be, for example, a 180 degree inversion pulse. Other inversion pulses may be employed. In other examples, the preparation phase may include a saturation pulse, RF energy configured to perform diffusion preparation in the volume, RF energy configured to perform T2 preparation in the volume, or RF energy configured to perform magnetization transfer preparation in the volume. To improve acquisition time, the Look-Locker pulse sequence may include two or more inversion recovery periods per preparation phase. The inversion recovery periods may be separated by a waiting period. In one example, the inversion recovery period may be 2.7 seconds and the pauses may be, for example, 3.5 seconds. Shorter or longer recovery periods or pauses may be employed.

In another embodiment, the Look-Locker pulse sequence may be a GRE pulse sequence. In one embodiment, a member of the two or more image acquisition units includes a flip-angle RF pulse of less than fifteen degrees and an EPI module. In one embodiment, the Look-Locker pulse sequence has a TE less than 1 ms and a TR less than 5 ms. In another embodiment, the Look-Locker pulse sequence has a TE less than 0.5 ms and a TR less than 3 ms. Other combinations of TE and TR may be employed.

Method 900 also includes, at 920, controlling the MRI apparatus to acquire a series of 3D data sets associated with NMR signals from the volume according to a non-Cartesian trajectory. The non-Cartesian trajectory may be, for example, a 3D stack-of-spirals trajectory, a 3D stack-of-stars trajectory, or other trajectory. In one embodiment, the MRI apparatus may be configured to acquire the series of 3D data sets using in-plane under-sampling at a factor of at least four. Other under-sampling reduction factors may be employed.

Method 900 also includes, at 930, controlling the MRI apparatus to reconstruct the series of 3D data sets into a corresponding series of 3D images using a 3D through-time non-Cartesian GRAPPA approach. Since the Look-Locker pulse sequence facilitates acquiring data from the volume in less than one breath hold, the series of 3D data sets may be reconstructed without performing view sharing. In one embodiment, the volume may be greater than 100 cubic centimeters, and NMR signals that cover the entire volume may be produced and acquired in less than 5 seconds. In another embodiment, the volume may be greater than 250 cubic centimeters, and NMR signals that cover the entire volume may be produced and acquired in less than 10 seconds. In other embodiments, NMR signals that cover less than the entire volume may be acquired.

Method 900 also includes, at 940, producing a 3D map of at least a portion of the volume based, at least in part, on one or more members of the series of 3D images. The map may be, for example, a T1 map, or other map. Since the Look-Locker pulse sequence facilitates acquiring data from the volume in less than one breath hold, the 3D map may not suffer from artifacts or other imperfections associated with movement in the volume. Thus, in one embodiment, the 3D map may be produced without performing B1 mapping. Similarly, the 3D map may be produced without performing image registration.

Method 900 also includes, at 950, displaying the 3D map. Displaying the 3D map may include providing images or data to a computer or other display device.

Method 900 also includes, at 960, producing a quantitative value for an MR parameter (e.g., T1 relaxation time) for the portion of the volume based, at least in part, on the 3D T1 map. The volume may be, for example, a human abdomen measuring greater than 500 cubic centimeters. In one embodiment, the NMR signals cover the entire volume and are produced and acquired in less than twenty seconds. While a human abdomen is described, other volumes of other sizes in humans and in other animals may be analyzed using method 900. While covering the entire volume is described, in one embodiment, NMR signals covering less than the entire volume may be acquired. Producing the quantitative value may include storing a value in a computer memory, updating a computer register, displaying a value, or other tangible action.

Figure 10:
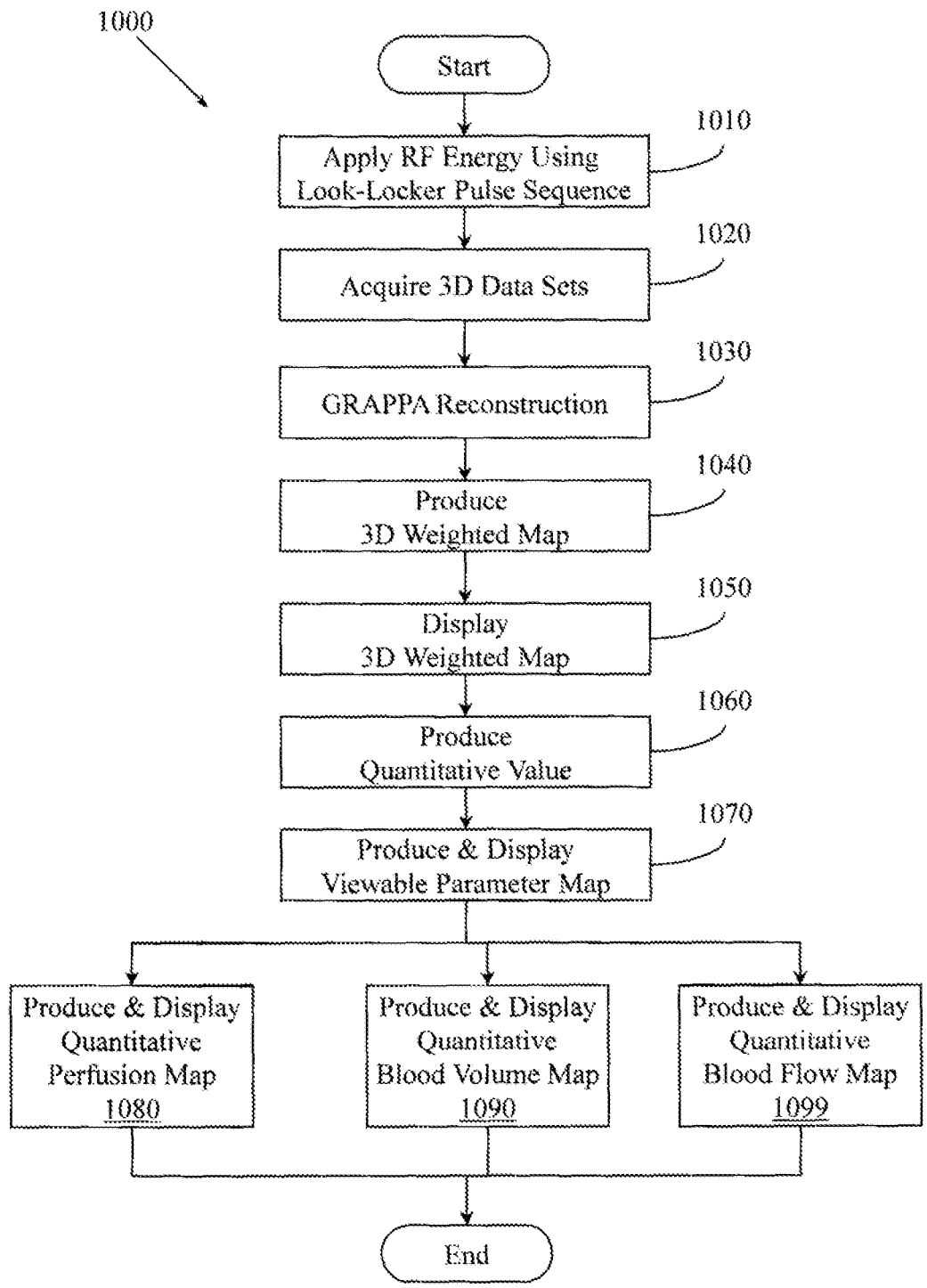
FIG. 10 illustrates a method associated with quantifying a magnetic resonance parameter using a Look-Locker method with 3D through-time non-Cartesian GRAPPA.

FIG. 10 illustrates a method 1000 associated with quantifying a magnetic resonance parameter using a Look-Locker method with 3D through-time non-Cartesian GRAPPA. Method 1000 includes several actions similar to those described in connection with method 900. For example, method 1000 includes applying RF energy using a 3D non-Cartesian Look-Locker pulse sequence at 1010, acquiring 3D data sets using a non-Cartesian trajectory at 1020, and performing 3D through-time non-Cartesian GRAPPA reconstruction at 1030. Similarly, method 1000 includes producing a 3D weighted map at 1040, displaying the 3D weighted map at 1050, and producing a quantitative value at 1060. However, method 1000 also includes additional actions.

For example, method 1000 includes, at 1070, producing and displaying a viewable parameter map. The viewable parameter map may be based, at least in part, on the 3D weighted map. In one embodiment, producing the viewable parameter map involves performing pixel-wise parameter mapping on the 3D weighted map. Since the NMR signals are acquired with less artifacts and other motion-related imperfections, the quantified value may be more precise. Thus, method 900 or method 1000 may produce the quantified value for the MR parameter with at least 50% precision, with at least 75% precision, or with even greater precision. "Precision", as used herein, refers to the quantified value agreeing with an actual value to within the described percentage. For example, if an actual T1 value was 100, then the quantified value would have at least 50% precision when the quantified value is within 50% of the actual value.

Producing the 3D weighted map facilitates producing other displayable quantitative maps. In one embodiment, method 1000 may include, at 1080, producing a quantitative perfusion map from the 3D weighted map. The quantitative perfusion map may display perfusion information associated with, for example, kidney perfusion, liver perfusion, or perfusion in another organ or region. In another embodiment, method 1000 may also include, at 1090, producing a quantitative blood volume map from the 3D weighted map. In yet another embodiment, method 1000 may also include, at 1099, producing a quantitative blood flow map from the 3D weighted map. While a perfusion map, a blood volume map, and a blood flow map are described, other quantitative maps may be produced and displayed.

While FIGS. 9 and 10 illustrate various actions occurring in serial, it is to be appreciated that various actions illustrated in FIGS. 9 and 10 could occur substantially in parallel. By way of illustration, a first process could acquire NMR signals, a second process could reconstruct the NMR signals, and a third process could produce quantified values. While three processes are described, it is to be appreciated that a greater and/or lesser number of processes could be employed and that lightweight processes, regular processes, threads, and other approaches could be employed.

In one example, a method may be implemented as computer executable instructions. Thus, in one example, a computer-readable storage medium may store computer executable instructions that if executed by a machine (e.g., processor) cause the machine to perform a method (e.g., method 900, method 1000). While executable instructions associated with the above method are described as being stored on a computer-readable storage medium, it is to be appreciated that executable instructions associated with other example methods described herein may also be stored on a computer-readable storage medium.

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the embodiments described herein. Therefore, the invention is not limited to the specific details, the representative apparatus, and illustrative examples shown and described. Thus, this application is intended to embrace alterations, modifications, and variations that fall within the scope of the appended claims.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and other similar exemplary language indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer component", as used herein, refers to a computer-related entity (e.g., hardware, firmware, software in execution, combinations thereof). Computer components may include, for example, a process running on a processor, a processor, an object, an executable, a thread of execution, and a computer. A computer component(s) may reside within a process and/or thread. A computer component may be localized on one computer and/or may be distributed between multiple computers.

"Computer-readable storage medium", as used herein, refers to a non-transitory medium that stores instructions or data. "Computer-readable storage medium" does not refer to propagated signals, per se. A computer-readable storage medium may take forms, including, but not limited to, non-volatile media, and volatile media. Non-volatile media may include, for example, magnetic disks, tapes, flash memory, ROM, and other media. Volatile media may include, for example, semiconductor memories, dynamic memory (e.g., dynamic random access memory (DRAM), synchronous dynamic random access memory (SDRAM), double data rate synchronous dynamic random-access memory (DDR SDRAM), etc.), and other media. Common forms of a computer-readable storage medium may include, but are not limited to, a floppy disk, a flexible disk, a hard disk, a magnetic tape, other magnetic medium, a compact disk (CD), other optical medium, a random access memory (RAM), a read only memory (ROM), a memory chip or card, a memory stick, and other media from which a computer, a processor or other electronic device can read.

"Data store", as used herein, refers to a physical and/or logical entity that can store data. A data store may be, for example, a database, a table, a file, a data structure (e.g. a list, a queue, a heap, a tree) a memory, a register, and other stores. In different examples, a data store may reside in one logical and/or physical entity and/or may be distributed between two or more logical and/or physical entities.

"Logic", as used herein, includes but is not limited to hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and other entities. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

"Signal", as used herein, includes but is not limited to, electrical signals, optical signals, analog signals, digital signals, data, computer instructions, processor instructions, messages, a bit, a bit stream, and other items, that can be received, transmitted and/or detected.

"Software", as used herein, includes but is not limited to, one or more executable instructions that cause a computer, processor, or other electronic device to perform functions, actions and/or behave in a desired manner. "Software" does not refer to stored instructions being claimed as stored instructions per se (e.g., a program listing). The instructions may be embodied in various forms including routines, algorithms, modules, methods, threads, and/or programs including separate applications or code from dynamically linked libraries.

"User", as used herein, includes but is not limited to one or more persons, software, logics, computers or other devices, or combinations of these.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, ABC, AAA, AAB, AABB, AABBC, AABBCC, (e.g., the data store may store only A, only B, only C, A&B, A&C, B&C, A&B&C, A&A&A, A&A&B, A&A&B&B, A&A&B&B&C, A&A&B&B&C&C). It is not intended to require one of A, one of B, and one of C. When the applicants intend to indicate "at least one of A, at least one of B, and at least one of C", then the phrasing "at least one of A, at least one of B, and at least one of C" will be employed.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

What is claimed is:

1. A method, comprising:
    controlling a magnetic resonance imaging (MRI) apparatus to apply radio frequency (RF) energy to a volume according to a non-Cartesian three-dimensional (3D) pulse sequence that is configured to cause the volume to produce nuclear magnetic resonance (NMR) signals, the pulse sequence comprising a preparation phase and two or more image acquisition units per preparation phase;
    controlling the MRI apparatus to acquire a series of 3D data sets of NMR signals from the volume according to a non-Cartesian trajectory;
    controlling the MRI apparatus to reconstruct the series of 3D data sets into a corresponding series of 3D images using a 3D through-time non-Cartesian generalized auto-calibrating partially parallel acquisitions (GRAPPA) approach;
    producing a 3D map of at least a portion of the volume based, at least in part, on one or more members of the series of 3D images, where the 3D map is weighted with respect to a magnetic resonance (MR) parameter, and
    producing a quantitative value for the MR parameter for the portion of the volume based, at least in part, on the 3D map.

2. The method of claim 1, where the volume is a portion of a human abdomen measuring greater than 500 cubic centimeters, where the NMR signals cover the entire volume, and where the NMR signals are produced and acquired in less than twenty seconds.

3. The method of claim 1, where the MR parameter is T1 relaxation, T2 relaxation, or diffusion.

4. The method of claim 3, where the pulse sequence is an inversion recovery Look-Locker pulse sequence.

5. The method of claim 4, where the preparation phase includes an inversion pulse, a 180 degree inversion pulse, a saturation pulse, RF energy configured to perform diffusion preparation, or RF energy configured to perform magnetization transfer preparation.

6. The method of claim 4, where the pulse sequence includes two or more inversion recovery periods separated by a waiting period.

7. The method of claim 3, where the pulse sequence is a gradient recalled echo (GRE) Look-Locker pulse sequence.

8. The method of claim 3, where the pulse sequence is a superfast Look-Locker pulse sequence.

9. The method of claim 3, where a member of the two or more image acquisition units includes a flip-angle RF pulse of less than fifteen degrees and an echo planar imaging module.

10. The method of claim 3, comprising controlling the MRI apparatus to acquire the series of 3D data sets using in-plane under-sampling at a reduction factor of at least four.

11. The method of claim 3, comprising producing the 3D map without performing B1 mapping.

12. The method of claim 3, comprising producing the 3D map without performing image registration.

13. The method of claim 3, where the non-Cartesian trajectory is a 3D stack-of-spirals trajectory.

14. The method of claim 3, where the non-Cartesian trajectory is a 3D stack-of-stars trajectory.

15. The method of claim 3, comprising reconstructing the series of 3D data sets without performing view sharing.

16. The method of claim 3, comprising producing and displaying a viewable parameter map of the MR parameter based, at least in part, on the 3D map.

17. The method of claim 16, where producing the viewable parameter map comprises performing pixel-wise parameter mapping on the 3D map.

18. The method of claim 1, comprising producing the quantified value for the MR parameter with at least 50% precision.

19. The method of claim 1, comprising producing the quantified value for the MR parameter with at least 75% precision.

20. The method of claim 1, where the volume is greater than 100 cubic centimeters, where the NMR signals cover the entire volume, and where the NMR signals are produced and acquired in less than 5 seconds.

21. The method of claim 1, where the volume is greater than 250 cubic centimeters, where the NMR signals cover the entire volume, and where the NMR signals are produced and acquired in less than 10 seconds.

22. The method of claim 1, where the pulse sequence has an echo time (TE) less than 1 ms and a repetition time (TR) less than 5 ms.

23. The method of claim 1, comprising producing a quantitative perfusion map from the 3D map.

24. The method of claim 1, comprising producing a quantitative blood volume map from the 3D map.

25. The method of claim 1, comprising producing a quantitative blood flow map from the 3D map.

26. An apparatus, comprising:
a processor;
a memory;
a set of logics, and
an interface to connect the processor, the memory, and the set of logics, the set of logics comprising:
  a first logic configured to control the application of radio frequency (RF) energy to a volume according to a three-dimensional (3D) Look-Locker (LL) pulse sequence comprising a preparation phase and multiple image acquisition units per preparation phase, where the pulse sequence is configured to cause the volume to produce nuclear magnetic resonance (NMR) signals;
  a second logic configured to acquire under-sampled 3D data associated with NMR signals from the volume according to a non-Cartesian acquisition trajectory;
  a third logic configured to reconstruct the under-sampled 3D data into reconstructed 3D data using 3D through-time non-Cartesian generalized auto-calibrating partially parallel acquisitions (GRAPPA), and a fourth logic configured to produce a quantified value for an MR parameter in at least a portion of the volume based, at least in part, on a signal intensity in the reconstructed 3D data, the MR parameter being T1 relaxation; and
  a fifth logic configured to produce a weighted map from the quantified value for the MR parameter without performing B1 mapping and without performing image registration.

27. The apparatus of claim 26, the non-Cartesian acquisition trajectory being a stack-of-spirals trajectory or a stack-of-stars trajectory.

28. The apparatus of claim 27, the Look-Locker pulse sequence being an inversion recovery sequence, or a gradient recalled echo (GRE) sequence.

29. The apparatus of claim 28, where the NMR signals are produced and acquired in less than ten seconds.

30. The apparatus of claim 29, where the second logic is configured to under-sample a partition in the volume by a reduction factor of at least four.

31. The apparatus of claim 26, where the fifth logic is configured to produce and display a viewable parameter map of the MR parameter.

32. The apparatus of claim 31, where the fifth logic is configured to produce a pixel-wise parameter map from the viewable parameter map.

33. The apparatus of claim 26, where the Look-Locker pulse sequence has an inversion time in the range of 240 ms to 2600 ms.

34. The apparatus of claim 33, where the Look-Locker pulse sequence has a repetition time (TR) of less than 4.5 ms and an echo time (TE) of less than 0.6 ms.

35. The apparatus of claim 34, where the Look-Locker pulse sequence has a flip angle (FA) of less than 8 degrees.

36. The apparatus of claim 35, where the Look-Locker pulse sequence has a partition thickness of less than 5 mm.

37. A magnetic resonance imaging apparatus, comprising:
means for acquiring nuclear magnetic resonance (NMR) signal data from a volume in response to radio frequency (RF) energy being applied to the volume according to a three-dimensional (3D) non-Cartesian Look-Locker magnetic resonance imaging (MRI) pulse sequence;
means for producing a quantified value of an NMR parameter in the volume from the NMR signal data based on data reconstructed from the NMR signal data using 3D through-time non-Cartesian generalized autocalibrating partially parallel acquisitions (GRAPPA), and
means for displaying an image that includes a representation of the quantified value,
where the NMR parameter is T1 relaxation.

\* \* \* \* \*